United States Patent
Sharkey

(10) Patent No.: US 9,486,320 B2
(45) Date of Patent: Nov. 8, 2016

(54) SUBCHONDRAL TREATMENT OF OSTEOARTHRITIS IN JOINTS

(71) Applicant: ZIMMER KNEE CREATIONS, INC., Exton, PA (US)

(72) Inventor: Peter F. Sharkey, Villanova, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 0 days.

(21) Appl. No.: 14/739,203

(22) Filed: Jun. 15, 2015

(65) Prior Publication Data

US 2015/0289983 A1    Oct. 15, 2015

Related U.S. Application Data

(63) Continuation of application No. 13/491,921, filed on Jun. 8, 2012, now abandoned.

(60) Provisional application No. 61/495,682, filed on Jun. 10, 2011.

(51) Int. Cl.

| A61F 2/40 | (2006.01) |
|---|---|
| A61F 2/32 | (2006.01) |
| A61F 2/38 | (2006.01) |
| A61F 2/36 | (2006.01) |
| A61B 17/68 | (2006.01) |
| A61B 17/86 | (2006.01) |
| A61F 2/30 | (2006.01) |
| A61B 17/16 | (2006.01) |
| A61B 17/74 | (2006.01) |
| A61B 17/70 | (2006.01) |
| A61B 17/88 | (2006.01) |

(52) U.S. Cl.
CPC ............ *A61F 2/3859* (2013.01); *A61B 17/68* (2013.01); *A61B 17/864* (2013.01); *A61F 2/32* (2013.01); *A61F 2/3601* (2013.01); *A61F 2/4003* (2013.01); *A61F 2/4059* (2013.01); *A61B 17/1668* (2013.01); *A61B 17/7098* (2013.01); *A61B 17/746* (2013.01); *A61B 17/8841* (2013.01); *A61F 2002/30235* (2013.01); *A61F 2002/30331* (2013.01); *A61F 2230/0069* (2013.01)

(58) Field of Classification Search
None
See application file for complete search history.

(56) References Cited

U.S. PATENT DOCUMENTS

| 5,514,137 A | 5/1996 | Coutts |
|---|---|---|
| 5,556,429 A | 9/1996 | Felt |

(Continued)

OTHER PUBLICATIONS

"U.S. Appl. No. 13/491,921, Final Office Action mailed Jan. 13, 2015", 8 pgs.

(Continued)

*Primary Examiner* — Sameh Boles
(74) *Attorney, Agent, or Firm* — Schwegman Lundberg & Woessner, P.A.

(57) ABSTRACT

Devices, instruments and associated methods for the subchondral treatment of osteoarthritis in hip and shoulder joints are provided. In addition, a method for treating joint pain is provided. The method comprises: identifying a subchondral defect in a subchondral region of a bone of the joint; selecting a subchondral access path to a location near the subchondral defect; and treating the subchondral defect, via the subchondral access, in a manner that restores normal force distribution and joint function while preserving the articular surface of the bone, wherein the joint is a hip or shoulder.

21 Claims, 8 Drawing Sheets

(56) References Cited

U.S. PATENT DOCUMENTS

| | | | |
|---|---|---|---|
| 5,755,809 A | 5/1998 | Cohen et al. | |
| 6,140,452 A | 10/2000 | Felt et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,306,177 B1 | 10/2001 | Felt et al. | |
| 6,395,007 B1 | 5/2002 | Bhatnagar et al. | |
| 6,564,083 B2 | 5/2003 | Stevens | |
| 6,607,561 B2 | 8/2003 | Brannon | |
| 6,613,054 B2 | 9/2003 | Scribner et al. | |
| 6,719,761 B1 | 4/2004 | Reiley et al. | |
| 6,746,451 B2 | 6/2004 | Middleton et al. | |
| 6,827,720 B2 | 12/2004 | Leali | |
| 6,863,899 B2 | 3/2005 | Koblish et al. | |
| 6,887,246 B2 | 5/2005 | Bhatnagar et al. | |
| 7,153,307 B2 | 12/2006 | Scribner | |
| 7,261,720 B2 | 8/2007 | Stevens et al. | |
| 7,708,742 B2 | 5/2010 | Scribner et al. | |
| 7,771,431 B2 | 8/2010 | Scribner et al. | |
| 7,811,290 B2 | 10/2010 | Rabiner | |
| 8,062,364 B1 | 11/2011 | Sharkey et al. | |
| 8,152,813 B2 | 4/2012 | Osorio et al. | |
| 8,168,692 B2 | 5/2012 | Wenz | |
| 2003/0138473 A1 | 7/2003 | Koblish et al. | |
| 2005/0119219 A1 | 6/2005 | Bellini et al. | |
| 2006/0064164 A1 | 3/2006 | Thelen et al. | |
| 2009/0157078 A1* | 6/2009 | Mikol | A61B 17/864 606/62 |
| 2010/0076503 A1 | 3/2010 | Beyar et al. | |
| 2010/0125240 A1* | 5/2010 | Spedden | A61B 17/0057 604/37 |
| 2010/0179549 A1 | 7/2010 | Keller et al. | |
| 2011/0004258 A1 | 1/2011 | Stone et al. | |
| 2011/0125156 A1 | 5/2011 | Sharkey et al. | |
| 2011/0125157 A1 | 5/2011 | Sharkey et al. | |
| 2011/0125264 A1 | 5/2011 | Bagga et al. | |
| 2011/0125265 A1 | 5/2011 | Bagga et al. | |
| 2011/0125272 A1 | 5/2011 | Bagga et al. | |
| 2012/0316571 A1 | 12/2012 | Sharkey | |

OTHER PUBLICATIONS

"U.S. Appl. No. 13/491,921, Non Final Office Action mailed Sep. 9, 2014", 7 pgs.

"U.S. Appl. No. 13/491,921, Response filed Jul. 18, 2014 to Restriction requirement mailed May 19, 2014", 7 pgs.

"U.S. Appl. No. 13/491,921, Response filed Dec. 9, 2014 to Non-Final Office Action mailed Sep. 9, 2014", 8 pgs.

"U.S. Appl. No. 13/491,921, Restriction Requirement mailed May 19, 2014", 7 pgs.

"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.

"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.

"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

* cited by examiner

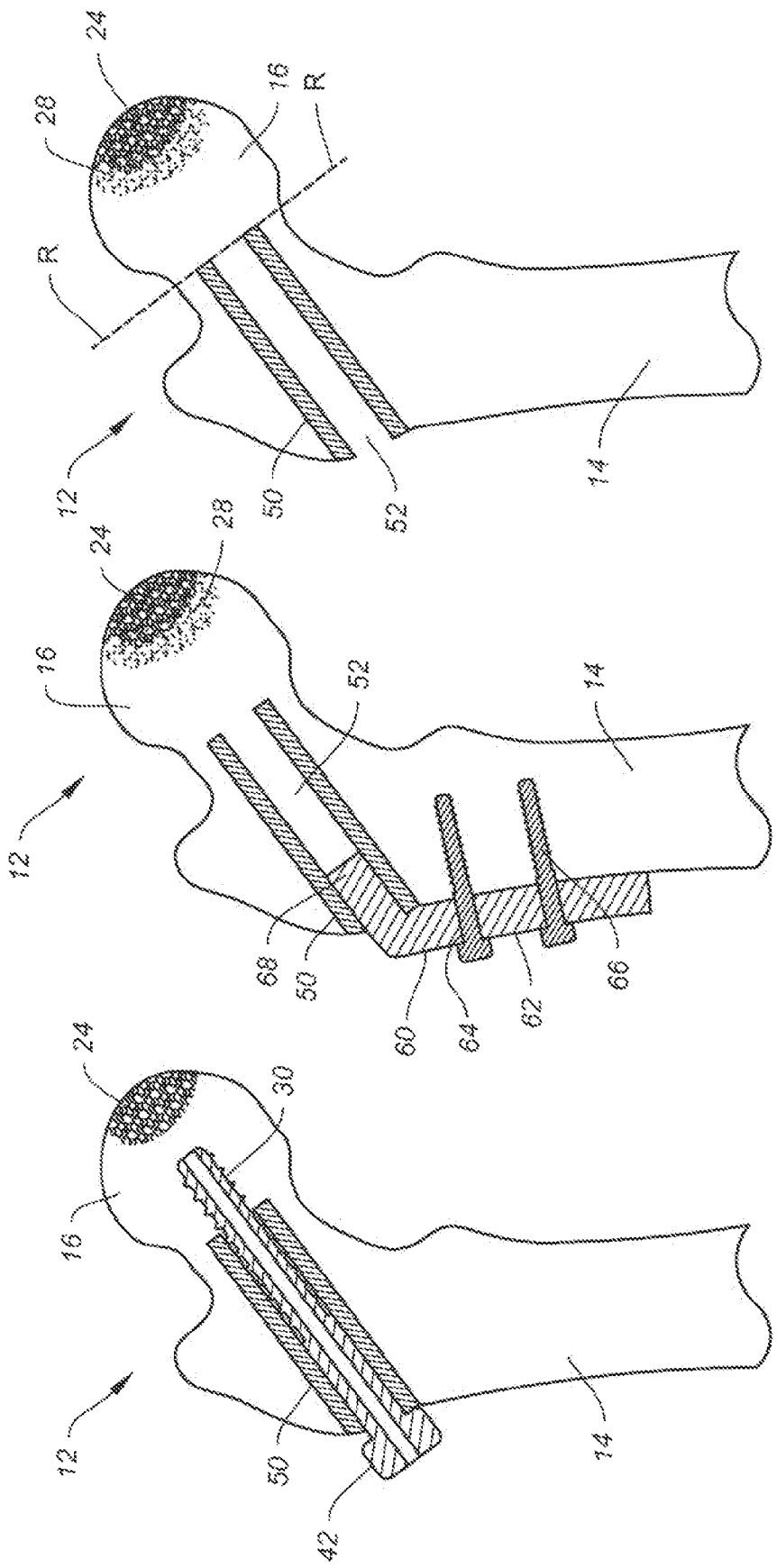

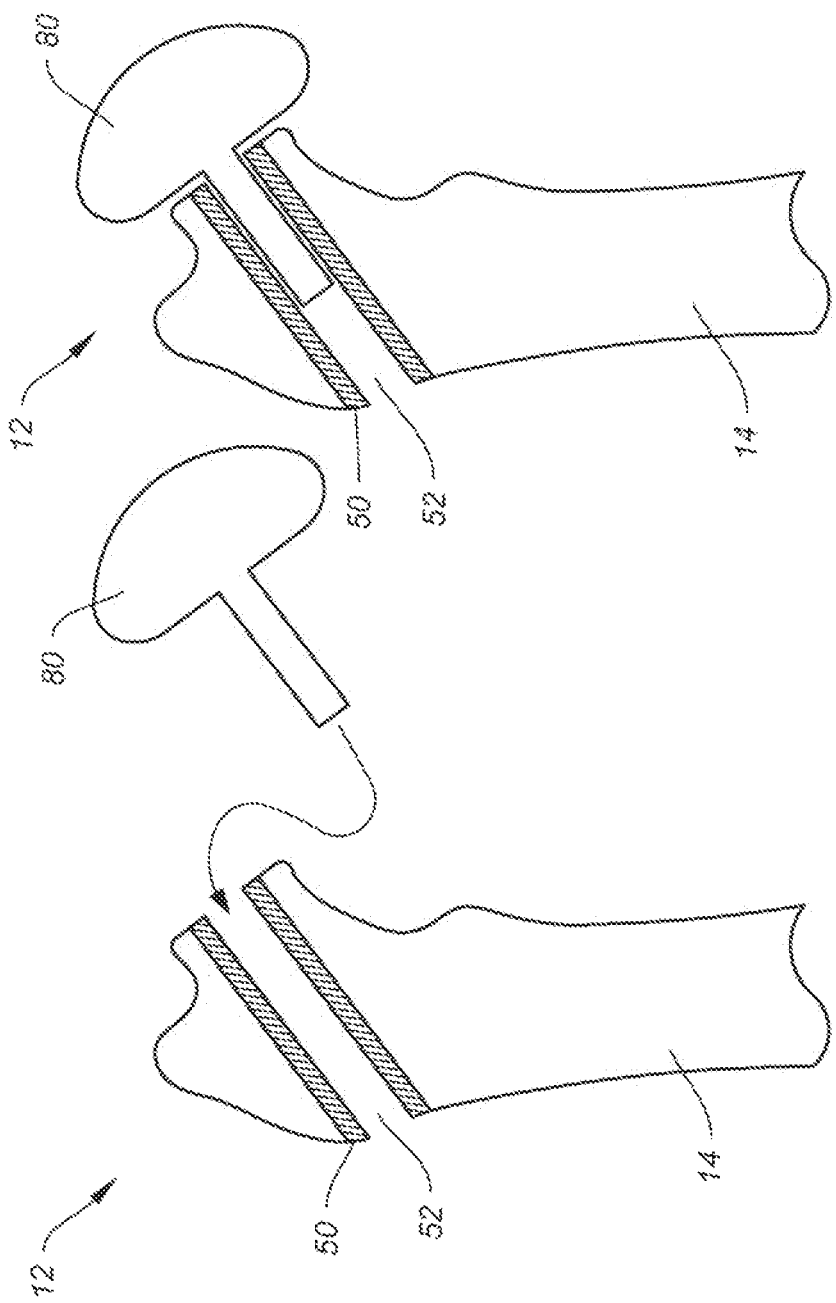

SUBCHONDRAL TREATMENT OF OSTEOARTHRITIS IN JOINTS

CROSS-REFERENCE TO RELATED APPLICATIONS

This application is a continuation of U.S. patent application Ser. No. 13/491,921 filed Jun. 8, 2012, which claims priority to U.S. Provisional No. 61/495,682 filed Jun. 10, 2011 and entitled "Subchondral Treatment of Osteoarthritis in the Hip and Should Joints," the content of each of which are incorporated by reference in its entirety.

FIELD

The present invention relates to devices and instruments for the surgical treatment of osteoarthritis at or near a joint, and more particularly to devices, instruments and associated methods for the subchondral treatment of osteoarthritis in hip and shoulder joints.

BACKGROUND

Human joints, in particular the knee, hip, shoulder, ankle, and spine, are susceptible to degeneration from disease, trauma, and long-term repetitive use that eventually lead to pain. Joint pain arising from arthritis, for example, is the impetus for a wide majority of medical treatments and associated medical costs. The most popular theory arising from the medical community is that joint pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, such as for example in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore normal joint function. Both non-surgical and surgical treatments are currently available for joint repair.

Non-surgical treatments can include weight loss (for the overweight patient), activity modification (low impact exercise), muscle strengthening, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

In the case of hips and shoulders, surgical options include partial hip or shoulder replacement, or total hip (THA) or total shoulder arthroscopy (TSA). Joint replacement surgery is often recommended for patients with severe pain associated with osteoarthritis, especially when other non-invasive options have failed. Both procedures have been shown to be effective in treating joint pain associated with osteoarthritis. However, patients only elect to undergo this type of surgery with reluctance. Both partial to total hip or shoulder arthroscopies are major surgical interventions and may be associated with severe complications. They are painful procedures that may require a long recovery. TKA patients often also report the replaced knee lacks a "natural feel" and have functional limitations. Moreover, both THA and TKA have limited durability. Accordingly, it would be desirable to provide a medical procedure that addresses the pain associated with osteoarthritis and provides an alternative to a THA, TSA or TKA procedure.

SUMMARY

The present disclosure provides devices, instruments and associated methods for the subchondral treatment of joint pain, and more specifically to devices, instruments and associated methods for the subchondral treatment of osteoarthritis in hip and shoulder joints.

In one embodiment, a method for treating joint pain is provided. The method comprises: identifying a subchondral defect in a subchondral region of a bone of the joint; selecting a subchondral access path to a location near the subchondral defect; and treating the subchondral defect, via the subchondral access, in a manner that restores normal force distribution and joint function while preserving the articular surface of the bone, wherein the joint is a hip or shoulder.

In another embodiment, a system for the treatment of osteoarthritis of a joint is provided. The system comprises a porous coated sleeve configured to cooperate with an injection bone screw. The system may be implanted into a bone of the joint such that the bone screw can be used to inject a bone hardening material into a subchondral space of the bone and around a subchondral defect. The bone screw may be removable, leaving the sleeve in place for future surgeries or for receiving an implant if desired.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 7A and 7B illustrate a method of treating a bone defect of a hip joint in accordance with still another embodiment of the present disclosure.

FIGS. 8A-8C illustrate a method of treating the bone defect of the hip joint of FIGS. 7A and 7B in accordance with yet another embodiment of the present disclosure.

DESCRIPTION OF THE EMBODIMENTS

Figure 1B:
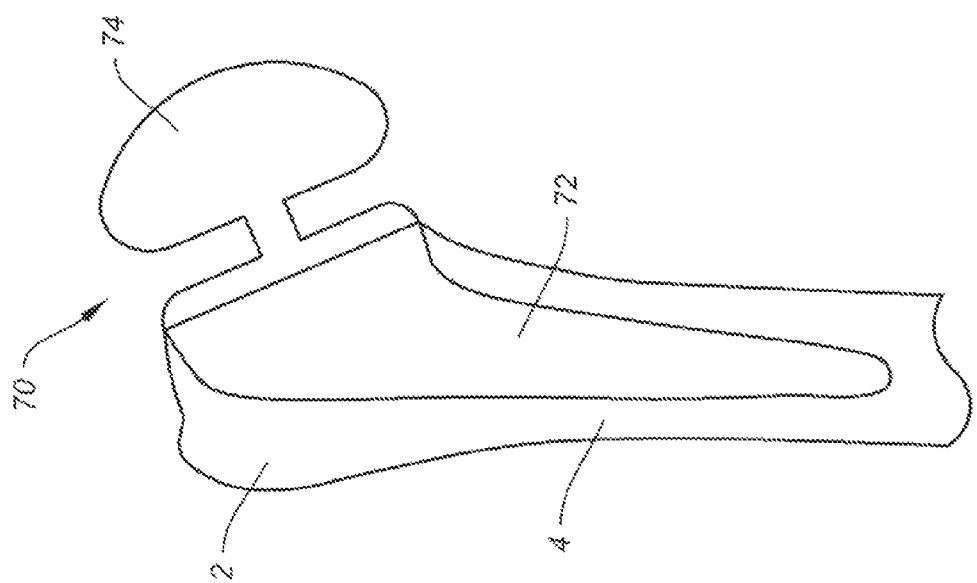
FIGS. 1A and 1B illustrate an exemplary method of shoulder replacement surgery of the prior art.

The present disclosure provides methodologies, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritis joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,384 entitled "OSTEOARTHRITIS TREATMENT AMD DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for SCP™ for the different extents of treatment needed can be employed. Accordingly, a medical practitioner may elect to use the techniques and devices described herein to subchondral treat any number of bone defects, as he deems appropriate.

Detection and identification of the relevant bone marrow lesion or bone marrow edema (BML or BME) can be achieved by imaging, e.g., magnetic resonance imaging (MRI), X-ray, bone scans, manual palpation, chemical or biological assay, and the like. A T1-weighted MRI can be used to detect sclerotic bone, for example. Another example is that a T2-weighted MRI can be used to detect lesions, edemas, and cysts. X-ray imaging maybe suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatment can be administered on acute stress fractures, BML or BME, or other subchondral defects, as previously mentioned.

The SCP™ treatment may continue after surgery. In particular, the patient may be monitored for a change in pain scores, or positive change in function. For example, patients are also checked to see when they are able to perform full weight-bearing activity and when they can return to normal activity. Of note, the SCP™ procedure can be revised and thus allows for optional further treatment in the event that a patient requires or desires a joint replacement or other type of procedure. The procedure does not exclude a future joint repair or replacement treatment to be applied, and thus may also be performed in conjunction with other procedures, such as cartilage resurfacing, regeneration or replacement, if desired. In those instances where additional treatment is desired, the SCP™ treated area may remain undisturbed while the additional treatment is performed, such as where cartilage resurfacing is desired. Alternatively, the SCP™ treated area can be removed, and not create an obstacle to the additional treatment, such as where a partial or total joint replacement is desired. Advantageously, the SCP™ treatment may be provided as a first or initial treatment, reserving for the future and possibly forestalling until a later date than otherwise might be the case more invasive treatments such as partial or total joint replacement.

A number of treatment modalities, and associated devices, instruments and related methods of use for performing SUBCHONDROPLASTY™ are disclosed in the aforementioned publications. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion. Preferably, the injection is made without disrupting the joint surface.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect (s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by reference. These devices and instruments can be use in combination with cements or hardening materials commonly used to repair damaged bone by their introduction into or near the site of damage, either to create a binding agent, cellular scaffold or mechanical scaffold for immobilization, regeneration or remodeling of the bone tissue. As previously stated, treatment of the bone defect at the subchondral level preferably is performed without disrupting the joint surface.

In general, the present disclosure provides embodiments related to instruments and associated methods for the surgical treatment of a joint, and particularly to a bone defect at that joint region. More specifically, the embodiments relate to instruments for navigating and positioning devices into an area sufficiently near a defect of the joint. Even more specifically, the instruments and associated methods for use are suitable for the repair of a femoral bone of a knee joint. These instruments and devices may be used in a manner consistent with the subchondral procedures previously described.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear outer degenerate locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level. If leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, restoration of normal physiologic stress distribution can be achieved in load bearing joints such as the hip and knee, and mechanical congruity restored, thereby resulting in healing of the inflammation and reduction or elimination of pain.

As previously mentioned, there is a need for surgical instruments that will facilitate the application of the methodologies described above at the target site, or the bone defect, to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area, and therefore require more precise defect location features. These instruments are also particularly suited to deliver bone substitute material, devices, implants, etc. without disrupting the joint surface. Accordingly, the present disclosure provides suitable instruments and associated methods for the surgical treatment of these bone defects, especially at the subchondral level near sclerotic bone.

In general, the present disclosure provides devices, instruments and associated methods for the subchondral treatment of osteoarthritis in hip and shoulder joints. Accordingly, embodiments of the present disclosure may be explained and illustrated with reference to treatment of a patient's shoulder or hip joint.

Figure 1A:
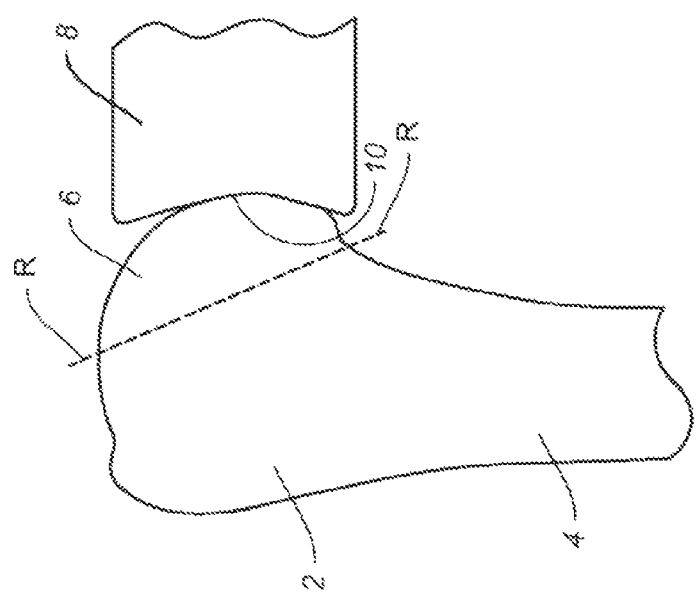

Referring now to FIGS. 1A and 1B, a shoulder joint is shown. The shoulder joint is a ball and socket joint that includes the humerus bone 2 and the glenoid bone 8. The humerus 2 comprises two main portions: the shaft 4 and the head 6 that articulates against the joint surface or cavity 10 of the glenoid 8. In a severely arthritic shoulder joint, pain can be treated by total shoulder replacement surgery, known as a total shoulder arthroscopy (TSA). As shown in FIG. 1A, in the first step of a standard TSA, the humerus 2 is resected along lines R-R to remove the damaged bone. Then, as shown in FIG. 1B, an implant 70 may be inserted into the humerus 2. The implant 70 may include a long stem 72 and an artificial head 74.

In most practices, the glenoid 8 doesn't always get resurfaced and so the new artificial head 74 may be called upon to articulate with the patient's natural glenoid 8. However where there is irreparable rotator cuff tearing or damage, an artificial ball or head may be used on the glenoid in what is commonly referred to as a total shoulder arthroscopy.

Figure 2:
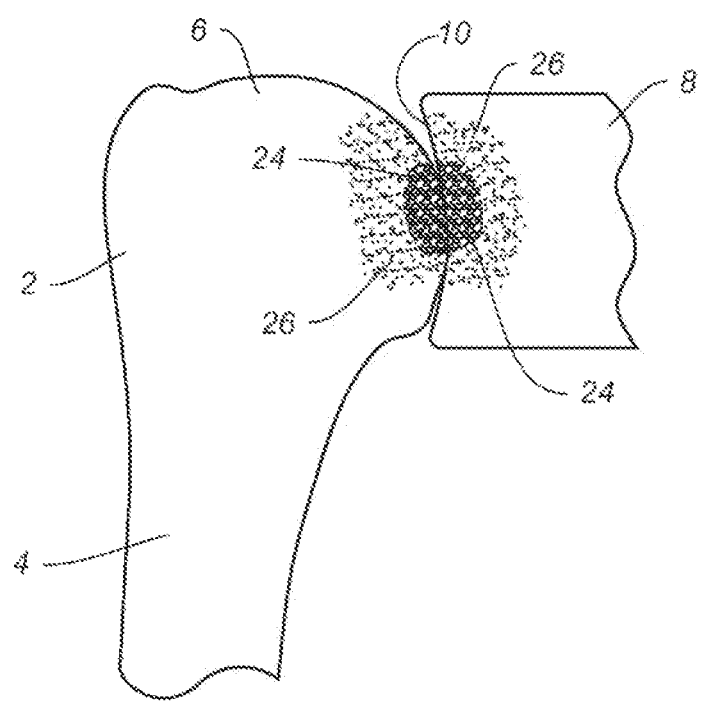
FIG. 2 illustrates an exemplary shoulder joint having a done defect on the head of the humerus and also on the glenoid cavity.

FIG. 2 illustrates an arthritic shoulder joint in which both the humeral head 6 and the glenoid 8 include bone defects. As has been observed, bone-on-bone arthritis of articular joints can often lead to "kissing lesions" where defects occur on both sides of the joint. As FIG. 2 represents, an osteoarthritis shoulder joint may result in a humeral head 6 having a sclerotic bone lesion 24 surrounding which can be a region 26 containing bone marrow edemas (BME) or bone marrow lesions (BML), most often in the subchondral region of the bone. The glenoid 8 may also include the same characteristics of a sclerotic bone lesion 24 surrounding which are BMEs or BMLs 26 on the opposite side of the articulating surface.

Figure 3A:
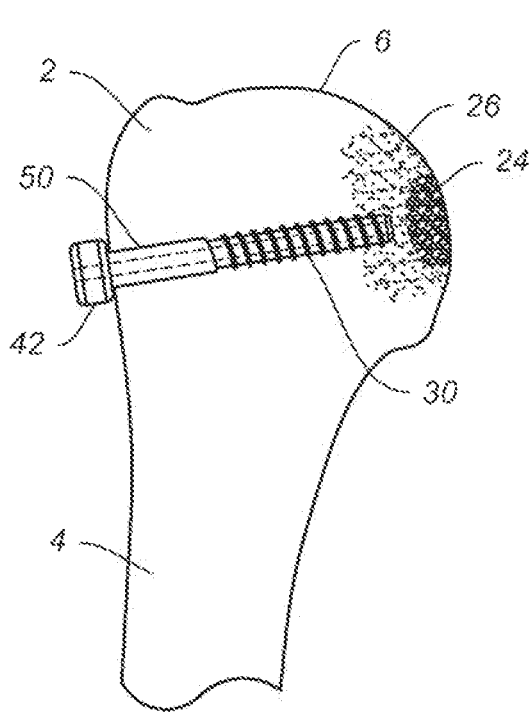
FIGS. 3A and 3B illustrate an exemplary method of treating a bone defect of the shoulder joint of FIG. 2.
Figure 3B:
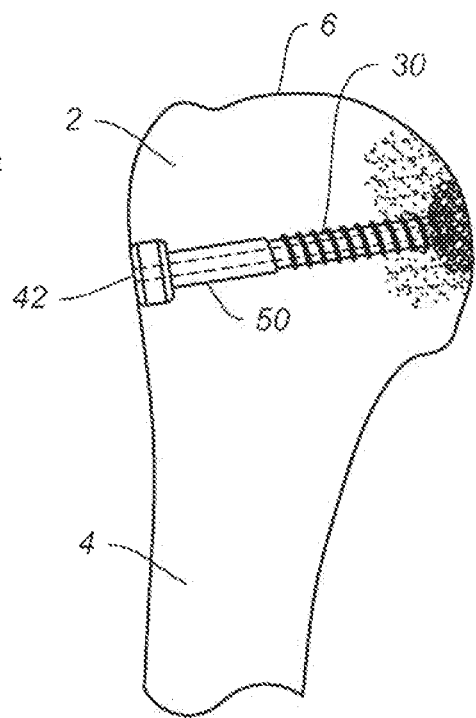
Figure 4:
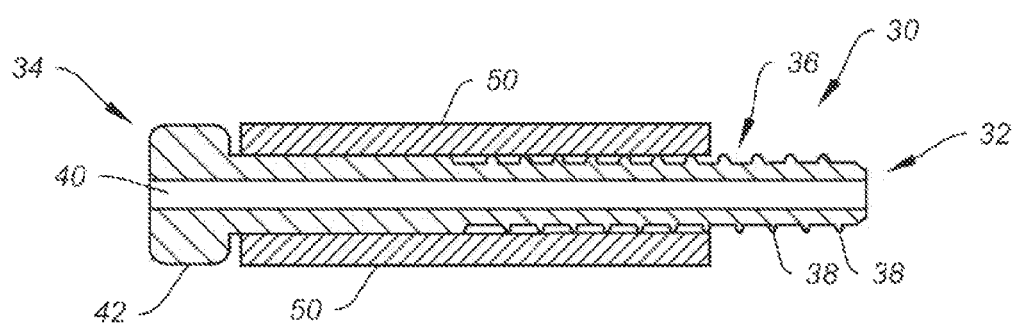
FIG. 4 illustrates a cross-sectional view of a sleeve and injection device system of the present disclosure.

FIGS. 3A and 3B illustrate exemplary embodiments for treating the bone defects of the shoulder joint. As shown, a delivery device in the form of an injectable bone screw 30 may be inserted into the humerus 2. The bone screw 30 may include a first, leading end 32, a second, trailing end 34 and an elongate shaft 36, as shown in greater detail in FIG. 4. The shaft 36 may include threads 38 to allow the bone screw to be threadedly engaged to the bone 2. A central channel 40 can be provided to allow for cannulation of the bone screw 30 so that material can be injected into the region. At the second, trailing end 34 the bone screw 30 can have a capped opening 42 that may rest proud against the bone surface, as shown in FIG. 3A, or may be entirely flush with the articular surface, as shown in FIG. 3B. The exterior surface of sleeve 50 may be treated or coated to promote bone ingrowth, in order to integrate the sleeve into the bone over time.

Surrounding the injectable bone screw 30 is a sleeve 50 that is configured to work with the injectable bone screw 30. The sleeve 50 may be porous and coated to allow for integration info the bone. When the screw 30 is used without the sleeve 50, the screw 30 including the capped opening 42 should be flush with the bone 2, to prevent soft tissue irritation from the capped opening 42. In another embodiment, a small cap (not shown) may be provided that can attach to the second, trailing end 34 of the screw 30 or the sleeve 50 if the screw is removed so that bone doesn't grow over the opening of the channel 40 or the sleeve, making it hard to find if later surgery is needed.

Figure 5A:
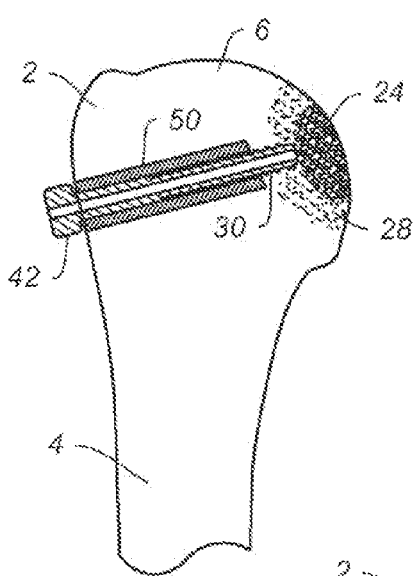
FIGS. 5A and 5B illustrate a method of treating a bone defect of the shoulder joint of FIG. 2 in accordance with one embodiment of the present disclosure.
Figure 5B:
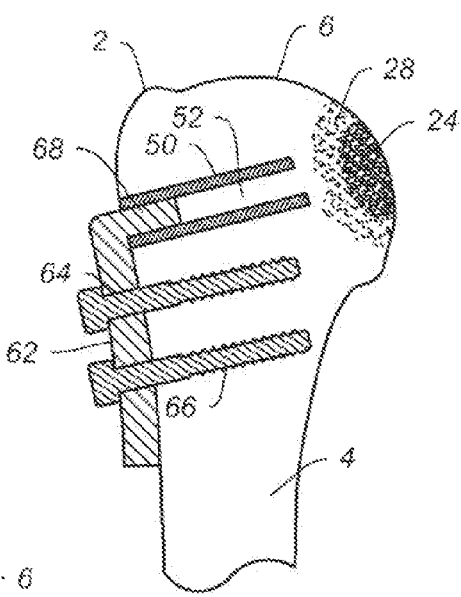

In one exemplary method of use, a guidewire is first inserted into the humerus using a visualization aid such as a fluoroscopic guidance system. An optional sleeve 50 may then be inserted over the guidewire into a drilled hole in the bone 2. The bone screw 30 may be inserted into the sleeve 50. An injectable material such as a bone substitute material (BSM) 28 may be injected through the bone screw 30 into the subchondral space and around the inflamed bone tissue (BME/BML), as shown in FIG. 5A. Ideally, the injected material would be a bone substitute material that could be fluoroscopically guided. After the material 28 is injected, the bone screw 30 may be removed. Sleeve 50 may be left in the bone after the subchondroplasty procedure. A bone defect of the glenoid may be treated by subchondroplasty in a similar manner.

Suitable injectable materials can include bone fillers, including but not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber, polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

It is contemplated that drilling into bone may potentially weaken the integrity and strength of the bone. Accordingly, in some cases it may be desirable to apply additional fixation such as a plate, particularly with weight bearing joints like the hip. In one embodiment, the sleeve 50 may be closed off by the insertion of a capped plate 60. As shown in FIG. 7B, the capped plate 60 may include a plate body 62, screw holes 64 for the insertion of screws 66 through the plate body 62 and info the bone 2, and a projection or finger 68 that can seat snugly within the sleeve 50. In the case of a hip joint, if may be desirable to attach one or more side plates (not shown) to prevent fractures in a high stress area and also improve fixation of any future total hip replacement.

The methods provided herein allow the user to with the option of still performing additional SCP™ procedures, partial or total joint replacement, or other revision surgeries, with relative ease. Since the sleeve 50 is intended to remain behind, it is contemplated that the sleeve 50 may be used to attach instruments or devices at a later time to perform these future surgeries. For example, the sleeve 50 may be used to attach a cutting guide to provide a clean, straight neck resection during a future arthroscopy. In addition, the sleeve 50 may also be an attachment mechanism to connect a fluoroscopic guidance system to assist if SUBCHONDROPLASTY™ is desired on the acetabulum of a hip joint or a glenoid of a shoulder joint, either during the initial procedure or in a future procedure. Additional BMEs may often develop at a later time on the acetabulum or glenoid alter the initial procedure to the femoral or humeral heads. The sleeve 50 would allow for easy access to these new BME's or BML's.

Figure 6A:
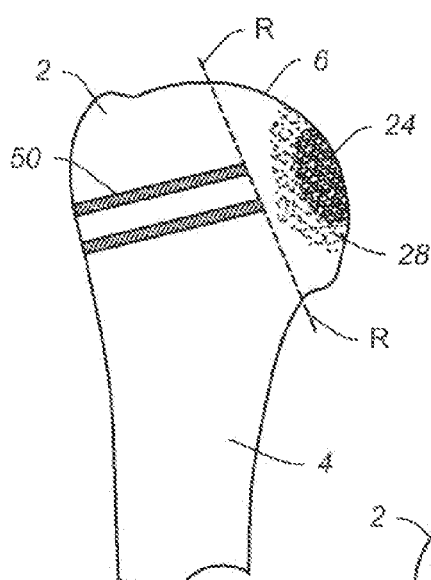
FIGS. 6A-6C illustrate a method of treating the bone defect of the shoulder joint of FIGS. 5A and 5B in accordance with another embodiment of the present disclosure.
Figure 6B:
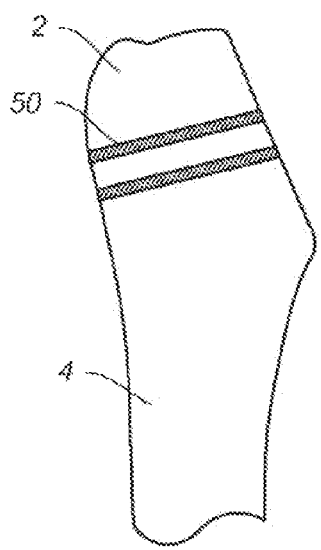
Figure 6C:
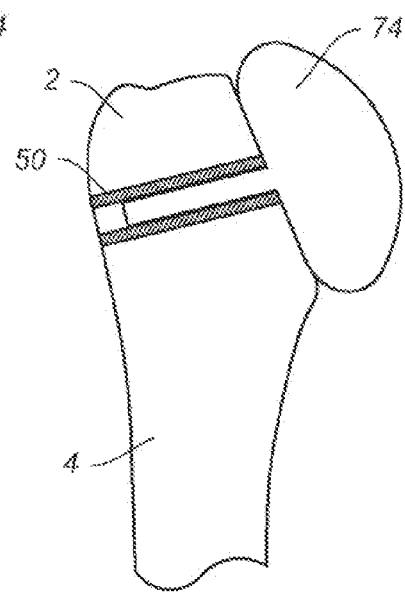

FIGS. 6A-6C illustrate an exemplary method in which the sleeve 50 has remained in and become integrated info the humerus 2 of the shoulder joint after an initial SCP™ procedure, and the osteoarthritis has continued to worsen, the patient continues to experience severe pain, or the surgeon otherwise believes a partial or total joint replacement is desirable. In this case, the surgeon may resect along lines R-R the disease portion of the humeral head 6, leaving in place the sleeve 50. If necessary, the central opening of the sleeve may be cleared of bone or tissue that may have infiltrated the channel after the first procedure and before the second procedure. The sleeve 50 may thus serve as an anchor for the humeral head replacement 74, with the implant 74 being inserted into the sleeve 50 as shown in FIG. 6C.

The sleeve 50 should ideally be as small as possible without sacrificing strength, while allowing a sufficiently large enough central channel for the insertion of future implants or guidance systems. The sleeve 50 should also provide optimal surface area for bone ingrowth and fixation, and should be easy to remove if needed. The configuration of the inside of the sleeve should also prevent any motion between the implant and the sleeve 50. By way of example, the interior of the sleeve and the stem of the implant may form a Morse taper.

FIGS. 7A and 7B illustrate methods of treating an osteoarthritis hip joint as previously described above in FIGS. 3A and 3B using the sleeve 50 and injectable bone screw 30 of the present disclosure. As FIG. 7A shows, the sleeve 50 and injectable bone screw 30 may be used in a femur 12 to treat a femoral head 16 having a subchondral defect 24 such as sclerotic bone tissue with the presence of BME/BMLs. FIG. 7B illustrates a method in which the bone screw 30 has been removed after an injectable material 28 has been injected around the subchondral bone defect 24, and an optional capped plate 60 is applied onto the sleeve 50 to cover up any openings. As previously stated, in hip joints with high stress areas additional fixation may be utilized, such as a side plate for additional stability.

Similar to the shoulder joint, the hip joint may also undergo additional SCP™ procedures, partial or total joint replacement, or other revision surgeries, with relative ease with the instruments of the present disclosure. As FIGS. 8A-8C illustrate, it is possible to perform a resection of the femoral head 16 along lines R-R in cases where a partial or total joint replacement is desired. Again the sleeve 50 that is in place may serve to attach a cutting guide to provide a clean, straight neck resection during a future hip arthroscopy. In addition, the sleeve 50 may attach to a fluoroscopic guidance system to assist if SUBCHONDROPLASTY™ is desired on the acetabulum, either during the initial procedure or in a future procedure. If necessary, the interior of the sleeve and the stem of the implant may form a Morse taper.

After resection, a femoral head implant 80 may be placed into the sleeve opening 52 of the sleeve 50 and secured to the sleeve, such as with a Morse taper. The opening 52 may then be capped as previously discussed, either with a cap or with a capped plate 60 similar to the one already described.

Figure 9:
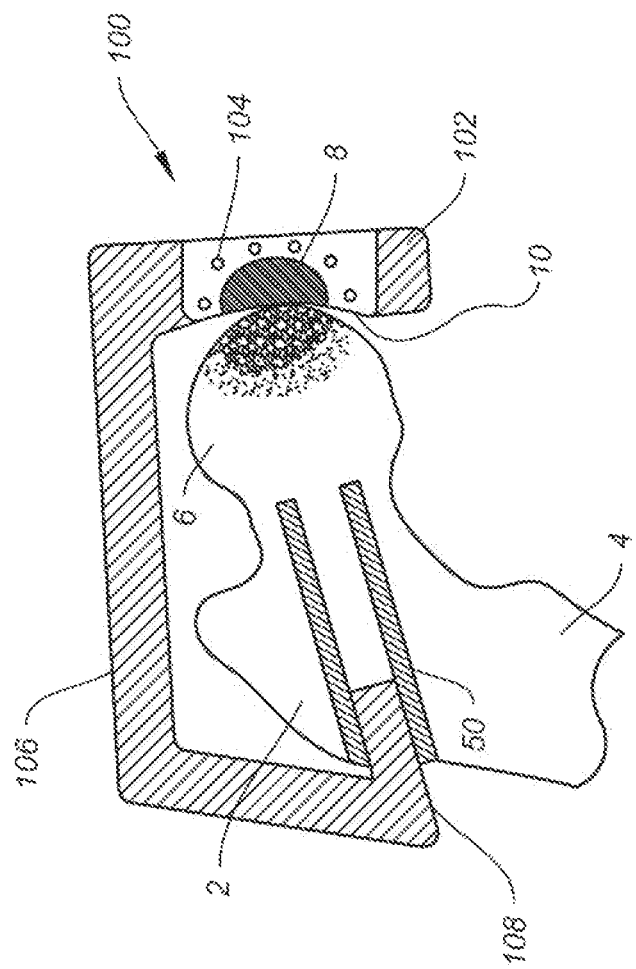
FIG. 9 illustrates a fluoroscopic guide system for treating a defect of an acetabulum of a hip joint.

FIG. 9 illustrates a method in which the sleeve 50 may attach to a fluoroscopic guidance system 100. As shown, the guidance system 100 may include a main body 102 from which extends an arm 106 having a projection or finger 108 for insertion into the opening 52 of the sleeve 50. The main body 102 may include one or more holes 104 suitable for guiding a guidewire, drill, pin, cannula or other associated delivery instrument therethrough. The main body 102 may be configured for placement against the acetabulum 8 to allow for a simultaneous or future SCP™ procedure to be performed on the acetabulum 8.

Other embodiments of the invention will be apparent to those skilled in the art from consideration of the specification and practice of the disclosure provided herein. By way of example, although the methods and apparatus described herein have been described in connection with treatment of the shoulder and hip, it is contemplated that the apparatus and techniques disclosed herein may be used with other joints, such as the elbow and ankle. It is intended that the specification and examples be considered as exemplary only, with a true scope and spirit of the disclosure being indicated by the following claims.

What is claimed is:

1. A method for a partial or total joint replacement in a patient, comprising:
resecting at least part of an end of a first bone adjacent a joint, wherein the end of the first bone has an articular surface that forms part of the joint, and wherein said resecting removes at least part of the articular surface and provides access to a first end of a sleeve that was implanted and left behind in the first bone in a prior surgical procedure that preserved the articular surface of the end of the first bone, said sleeve being fixed to surrounding bone via bone ingrowth into the sleeve; and
positioning part of a joint prosthesis in the first end of the sleeve for anchoring the joint prosthesis in the first bone.

2. The method of claim 1, wherein the joint is a shoulder joint or a hip joint, and the first bone is a humerus or a femur, respectively.

3. The method of claim 1, wherein the first end of the sleeve is located in a neck of the femur or a neck of the humerus.

4. The method of claim 1 further comprising delivering a bone void filler through the sleeve prior to said resecting.

5. A method for a partial or total joint replacement in a patient, comprising:
re-accessing a sleeve in an end of a first bone adjacent a joint, the sleeve having been implanted and left behind in the first bone in a prior surgical procedure, wherein the re-accessed sleeve is fixed to surrounding bone via bone ingrowth into the sleeve;
resecting at least part of the end of the first bone, wherein said resecting exposes a first end of the fixed sleeve and includes operation of a cutting instrument and/or cutting guide attached to the fixed sleeve; and
positioning part of a joint prosthesis in the first end of the fixed sleeve for anchoring the joint prosthesis in the first bone.

6. The method of claim 5, wherein said re-accessing includes re-accessing a second end of the sleeve.

7. The method of claim 6 further comprising removing a cap from the second end of the sleeve.

8. The method of claim 5, wherein the end of the first bone has an articular surface that forms part of the joint, and wherein said prior surgical procedure preserved the articular surface of the end of the first bone.

9. The method of claim 5, wherein the first end of sleeve is shaped for making a Morse taper connection.

10. The method of claim 5, wherein said prior surgical procedure included delivering a bone void filler through the sleeve.

11. A method for a partial or total joint replacement in a patient, comprising:
re-accessing a sleeve in an end of a first bone adjacent a joint, the sleeve having been implanted and left behind in the first bone in a prior surgical procedure, wherein said sleeve is fixed to surrounding bone via bone ingrowth into the sleeve, and wherein said re-accessing includes removing at least part of the end of the first bone and exposing a first end of the sleeve; and
positioning part of a joint prosthesis in the first end of the re-accessed sleeve for anchoring the joint prosthesis in the first bone.

12. The method of claim 11 further comprising removing a cap from a second end of the re-accessed sleeve.

13. The method of claim 11 further comprising removing a cannulated bone screw from the sleeve prior to said positioning.

14. The method of claim 11, wherein the joint is a shoulder, hip, knee or ankle joint.

15. The method of claim 11, wherein said positioning includes positioning a stem component of the joint prosthesis in the first end of the re-accessed sleeve.

16. The method of claim 11, wherein the end of the first bone has an articular surface that forms part of the joint, and wherein said prior surgical procedure preserved the articular surface of the end of the first bone.

17. The method of claim 16, wherein said prior surgical procedure was used to treated a bone marrow lesion or a bone marrow edema in the first bone.

18. The method of claim 11, wherein said resecting includes operation of a cutting instrument and/or cutting guide attached to the re-accessed sleeve.

19. The method of claim 11, wherein the sleeve is porous coated.

20. The method of claim 11, wherein the sleeve is porous.

21. The method of claim 11, wherein the joint prosthesis and the sleeve are connected via a Morse taper connection.

* * * * *